United States Patent [19]

Hatfield et al.

[11] 4,226,986

[45] Oct. 7, 1980

[54] PROCESS FOR HALOGENATION OF β-LACTAM COMPOUNDS

[75] Inventors: Lowell D. Hatfield, Bargersville; Larry C. Blaszczak; Jack W. Fisher, both of Indianapolis, all of Ind.

[73] Assignee: Eli Lilly and Company, Indianapolis, Ind.

[21] Appl. No.: 8,647

[22] Filed: Feb. 1, 1979

[51] Int. Cl.² ............................................. C07D 501/04
[52] U.S. Cl. ................................. 544/16; 260/239 A; 544/21; 544/22; 548/153
[58] Field of Search .............................. 544/22, 16, 21

[56] References Cited

U.S. PATENT DOCUMENTS

| | | | |
|---|---|---|---|
| 3,925,372 | 12/1975 | Chauvette | 544/16 |
| 3,962,227 | 6/1976 | Chauvette | 544/16 |
| 4,115,643 | 9/1978 | Kukolja et al. | 544/16 |

*Primary Examiner*—Nicholas S. Rizzo
*Attorney, Agent, or Firm*—Steven R. Lammert; Arthur R. Whale

[57] ABSTRACT

Novel halogenating compounds, derived from triaryl phosphites and chlorine or bromine are employed to convert 7-acylamino-3-hydroxy-3-cephem compounds to 7-acylamino-3-halo-3-cephems and the corresponding C-7 imino halide cephem derivatives. The product 3-halo-3-cephems are antibiotic compounds or intermediates thereto.

38 Claims, No Drawings

PROCESS FOR HALOGENATION OF β-LACTAM COMPOUNDS

BACKGROUND AND SUMMARY OF THE INVENTION

An intensive research effort in the field of cephalosporin antibiotics has produced a number of clinically significant cephalosporin compounds. One of the more recent developments in this area has been the discovery of cephem compounds directly substituted with halogen at the C-3 position. A number of 3-halo-3-cephems have been described by Chauvette in U.S. Pat. Nos. 3,925,372, 4,064,343 and 3,962,227. These potent antibiotic compounds are prepared by halogenation of the corresponding 3-hydroxy-3-cephems. The halogenation of 3-hydroxy-3-cephems to provide 3-chloro and 3-bromo-3-cephems has typically been carried out by reacting the 3-hydroxy-3-cephem compounds with brominating or chlorinating agents including phosgene, oxalyl chloride, thionyl chloride, thionyl bromide and phosphorous halides such as phosphorous trichloride and phosphorus tribromide, usually in the presence of dimethylformamide.

This invention is directed to a process for preparing 3-halo-3-cephems and related thiazoline azetidinone vinyl halides utilizing novel halogenating reagents.

More particularly this invention is directed to a process for halogenating 7-acylamino 3-hydroxy 3-cephem compounds with novel halogenating compounds of the general formula

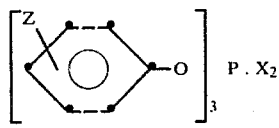

wherein Z is hydrogen, halo, $C_1-C_4$ alkyl or $C_1-C_4$ alkoxy, and X is Cl or Br, which halogenating compounds are the kinetically controlled products of the reaction of equivalent amounts of a triaryl phosphite of the formula

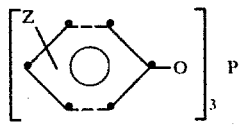

and chlorine or bromine in a substantially anhydrous inert organic solvent. The products of the present process are 7-acylamino-3-chloro-3-cephem compounds or, depending on the reaction conditions selected, the corresponding 3-chloro-3-cephem imino halides which are easily converted to the related 7-amino-3-chloro-3-cephem derivatives. The 3-halo-3-cephems are known antibiotics or are intermediates thereto.

In another embodiment of this invention novel thiazolineazetidinone vinyl halide compounds of the formula

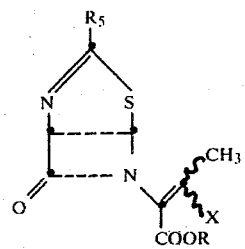

are prepared from the corresponding enols of the formula

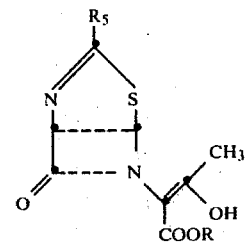

utilizing the aforedescribed novel halogenating reagents. The thiazolineazetidinone vinyl halides (R=H) have been found to exhibit antibacterial activity.

DETAILED DESCRIPTION OF THE INVENTION

Triaryl phosphites of the formula

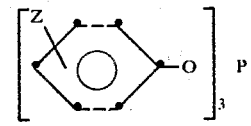

wherein Z is hydrogen, halo, $C_1-C_4$ alkyl or $C_1-C_4$ alkoxy, have been found to react with equivalent amounts of chlorine or bromine in a substantially anhydrous inert organic solvent to provide, initially, kinetically controlled products having the empirical formula

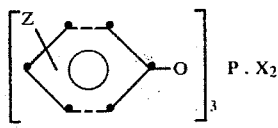

wherein Z is as defined above and X is Cl or Br.

The term "halo" in the definition of Z includes chloro, bromo or iodo. "$C_1-C_4$ Alkyl" includes methyl, ethyl, isopropyl, n-propyl, n-butyl, sec-butyl, tert-butyl and isobutyl. Representative "$C_1-C_4$ alkoxy" groups are methoxy, ethoxy, isopropoxy, tert-butoxy and n-butoxy.

The dot (.) in the general formula used to represent the kinetically controlled products employed in the present processes is used simply to designate that equivalent amounts of halogen and triarylphosphite are combined chemically and in a way that can be distinguished from that in the thermodynamically stable derivatives which have been known in the art and which typically have been drawn without the dot [e.g. (PhO)₃PCl₂]. The exact molecular form of the tiaryl phosphite-halogen kinetic complexes described herein has not been established definitively; however, physical-chemical data do indicate that the kinetic product is one wherein the phosphorous center acquires some cationic character. Herein the terms "kinetic compound", "kinetic complex", "triarylphosphite-halogen complex (compound)", "kinetically controlled products and "kinetically controlled halogenating compounds" are used synonomously.

Suitable triarylphosphites for the preparation of the kinetically controlled halogenating compounds used in the present process include triphenyl phosphite, tri(p-methoxyphenyl)phosphite, tri(o-chlorophenyl)phosphite, tri(p-chlorophenyl)-phosphite, tri(p-tolyl)phosphite, tri(o-tolyl)phosphite, tri(m-bromophenyl)phosphite, tri(p-bromophenyl)phosphite, tri(p-iodophenyl)phosphite, tri-(p-n-propylphenyl)phosphite, tri(p-tert-butylphenyl)-phosphite, tri(m-tolyl)phosphite, tri(p-isopropoxyphenyl)phosphite and the like. Triphenyl phosphite is preferred, primarily because of commercial availability.

Any of a wide variety of inert organic solvents may be employed as the medium for the preparation of the kinetically controlled halogenating compounds and for the halogenation processes described below. By "inert organic solvent" is meant an organic solvent which, under the reaction conditions of the preparation, does not enter into any appreciable reaction with either the reactants or the products. Since the halogenating compounds are susceptible to reaction with protic compounds, such compounds, including water, alcohols, amines (other than tertiary), thiols, organic acids and other such protic compounds should be excluded from the reaction medium.

A substantially anhydrous aprotic organic solvent is preferred. The term "substantially anhydrous" as used in the present description means that, although anhydrous organic solvents are generally preferred, trace amounts of water, such as that often found in commercially available solvents, can be tolerated. Although the kinetic products described herein will react with any water present in the solvent medium, additional amounts of reagents can easily be added to compensate for the loss due to hydrolysis. It is preferred that conventional laboratory techniques be employed to dry the solvents employed and to exclude moisture from the reaction mixtures.

Suitable solvents include hydrocarbons, both aliphatic and aromatic, including pentane, hexane, heptane, octane, cyclohexane, cyclopentane, benzene, toluene, o-, m- or p- xylene, mesitylene and the like; ethers, cyclic and acyclic such as diethyl ether, butyl ethyl ether, tetrahydrofuran, dioxane, 1,2-dimethoxyethane and the like; carboxylic acid esters such as ethyl acetate, methylformate, methyl acetate, amyl acetate, n-butyl acetate, sec-butyl acetate, methyl propionate, methyl butyrate and the like; nitriles such as acetonitrile, propionitrile, butyronitrile and the like; halogenated hydrocarbons, both aromatic and aliphatic, such as chloroform, methylene chloride, carbon tetrachloride, 1,2-dichloroethane (ethylene dichloride), 1,1,2-trichloroethane, 1,1-dibromo-2-chloroethane, 2-chloropropane, 1-chlorobutane, chlorobenzene, fluorobenzene, o-, m-, or p- chlorotoluene, o-, m-, or p-bromotoluene, dichlorobenzene and the like; and nitro compounds such as nitromethane, nitroethane, 1- or 2-nitriopropane, nitrobenzene and the like.

The particular inert organic solvent employed as a medium for the preparation of the kinetically controlled triaryl phosphite-halogen compounds or as a medium for their use in the present halogenation processes is not critical, however, such solvent properties as polarity, melting or boiling point, and ease of isolation of halogenated products may be considered in selecting a most suitable solvent.

Preferred solvents for the preparation of the kinetically controlled products and for the present processes described hereinbelow are hydrocarbons, especially aromatic hydrocarbons, and halogenated hydrocarbons.

If a halogenating compound derived from the kinetically controlled reaction of a triaryl phosphite and chlorine or bromine is allowed to stand in solution it converts or isomerizes to the corresponding thermodynamically stable compound at varying rates depending on, among other things, the nature of the tiaryl phosphite, the solvent, the halogen and the solution temperature. Experimental data has also shown that the presence of an acid (HX) or an excess of triaryl phosphite will enhance the rate of conversion of the kinetic to the thermodynamic product.

Using $^{31}P$ nuclear magnetic resonance spectroscopy the half-life of the kinetically controlled product from the reaction of triphenyl phosphite and chlorine in methylene chloride at room temperature was determined to be about 8 hours. A half-life of about 39 hours was observed for the triphenyl phosphite-bromine kinetic complex under the same conditions. As mentioned above the observed half-life (rate of conversion) for any given kinetic complex described herein can be affected by the solvent and by the presence of a hydrogen halide acid (HX) or excess triaryl phosphite. Thus, for example, a shorter half-life will be observed where the solvent for the preparation of kinetic complex has not been rigorously dried; the hydrogen halide acid produced from reaction of the kinetic complex with the moisture present in the solvent will enhance the rate of conversion to the stable form. Table I presents a summary of several properties of the kinetically controlled product and the corresponding thermodynamically controlled product of the reaction of triphenyl phosphite and chlorine.

TABLE I

| Kinetic product | Thermodynamic product |
|---|---|
| 1. $^{31}P$ nmr (CH₂Cl₂) − 3.7 ppm* | 1. $^{31}P$ nmr (CH₂Cl₂) + 22.7 ppm* |
| 2. $t_{\frac{1}{2}} = \simeq$ 8 hours at room temperature in methylene chloride | 2. Stable at room temperature |
| 3. ir (CH₂Cl₂) 1120–1190 (vs), 1070 (vs), 1035 (s), 1010 (vs), 990 (vs), 640 (m), 625 (m), 580 (w), 510 (s), 465 (w).** | 3. ir (CH₂Cl₂) 1130–1210 (vs), 1065 (vs), 1035 (s), 1010 (vs), 980 (vs), 625 (vw), 590 (m), 505 (s) 460 (s).** |
| 4. Hydrolyzes to give HCl and | 4. Hydrolyzes to give inter alia HCl, |

TABLE I-continued

| Kinetic product | Thermodynamic product |
|---|---|
| (PhO)₃PO | PhOH (phenol) and (PhO)₂PCl |
| 5. Reacts with n-BuOH to give HCl, n-BuCl and PhO₃PO | 5. Reacts with n-BuOH to give HCl, PhOH (phenol), n-BuCl and (PhP) — (BuO)$_b$ POCl$_c$, wherein a,b,c, = $0^a$, 1, 2 or 3 and a + b + c = 3 |

*Relative to $^{31}$P of H₃PO₄; (+) indicates upfield shift; (−) indicates downfield shift
**vs = very strong, s = strong, m = medium, w = weak The term kinetically controlled product is a term of art which when used in reference to reactions yielding two (or more) products, refers to the product formed faster, regardless of its thermodynamic stability. If such a reaction is stopped well before the products achieve thermodynamic equilibrium, the reaction is said to be kinetically controlled since more of the faster formed product will be present. In some cases, including the reaction of triaryl phosphites and chlorine or bromine, the rate of formation of the kinetic product and the rate of thermodynamic equilibrium is such that the kinetically controlled product can be prepared and utilized before any significant amount of the kinetically controlled product equilibrates or isomerizes to the thermodynamically stable product.

To maximize the production and stability of the kinetically controlled product, reaction conditions are selected so as to minimize the potential for thermodynamic equilibrium of the initial product of the reaction. Most simply conditions for kinetic control are achieved by lowering the reaction temperature and the temperature of the kinetic product after it is formed, and by minimizing the time allowed for thermodynamic equilibrium, such as, by utilizing the kinetic product in a subsequent reaction shortly after it has been prepared.

Typically the reactants, a triaryl phosphite and chlorine or bromine, are combined in a substantially anhydrous inert organic solvent at a temperature below about 30° C. Although the kinetically controlled products are formed at higher temperature, such conditions favor the formation of the thermodynamically controlled products. Preferably the halogenating compounds are prepared at temperatures at or below about 30° C. Minimum reaction temperature are, of course, determined by the freezing point of the solvent employed for the preparation. Most preferred reaction temperatures are in the range of about −70° to about 0° C.

It has been found that the triaryl phosphite itself reacts to some extent with its kinetic reaction product with chlorine or bromine, effectively increasing the rate of conversion to the corresponding thermodynamic product. It is preferred, therefore, but not required, that an excess of halogen be maintained in the reaction mixture during the formation of the halogenating compounds. This can be achieved practically by adding the triaryl phosphite to a solution of an equivalent amount of the halogen or by adding the halogen and the triaryl phosphite simultaneously to a quantity of inert organic solvent at the desired temperature. The co-addition of the reagents is conducted at such a rate that the color of the halogen persists in the reaction mixture until the last drop of triaryl phosphite discharges the color. Alternatively excess halogen can be discharged using known halogen scavengers such as acetylenes, or olefins including alkenes, dienes, cycloalkenes, or bicycloalkenes. A preferred scavenger is a C₂ to C₆ alkene, for example, ethylene, propylene, butylene, or amylene.

The kinetically controlled halogenating reagents used in the process of the present invention are stabilized in solution by the addition of about 10 to about 100 mole percent of a tertiary amine base having a pK$_b$ value of about 6 to about 10. If, for example, about 50 mole percent of pyridine is added to a solution of the kinetically controlled product of the reaction of triphenyl phosphite and chlorine in methylene chloride, only trace amounts of the thermodynamic equilibrium product can be detected by $^{31}$P nmr, even after prolonged periods at room temperature. The tertiary amine base can be added to a solution of the freshly prepared chlorinating compound or, optionally, it can be employed in the reaction mixture of the triaryl phosphite and halogen to produce a stabilized solution of the kinetically controlled product of the present invention.

One embodiment of the present invention is a process for preparing a compound of the formula

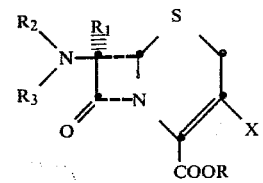

which comprises reacting a compound of the formula

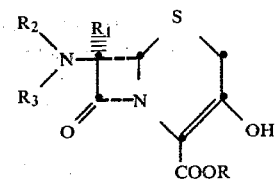

with about 1.0 to about 1.3 equivalents of one of the aforedescribed halogenating compounds of the general formula

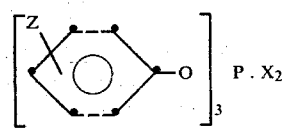

in a substantially anhydrous inert organic solvent at a temperature below about 30° C. wherein in the above formulas
X is Cl or Br;
Z is hydrogen, halo, C₁–C₄ alkyl, or C₁–C₄ alkoxy;
R is a carboxylic acid protecting group;
R₁ is hydrogen or methoxy;

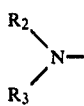

is amino protected by a conventional amino protecting group; or

R₂ is hydrogen or an acyl group derived from a carboxylic acid, and

R₃ is an acyl group derived from a carboxylic acid; or

R₂ and R₃ taken together with the nitrogen atom to which they are attached form a group of the formula

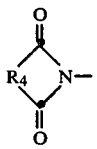

wherein R₄ is the residue of an acyl group derived from a dicarboxylic acid; provided that when R₂ and R₃ are substituted by amino, hydroxy or carboxy groups, those groups are first protected by one of the conventional amino, hydroxy or carboxy protecting groups.

In another but analogous process embodiment of the present invention novel thiazoline azetidinone vinyl halides of the formula

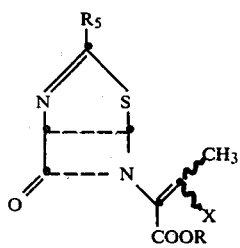

also an embodiment of the present invention, are prepared by reacting a compound of the formula

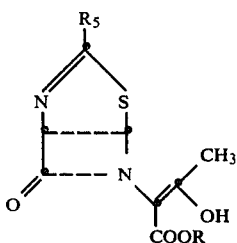

with the same halogenating reagents and under the same conditions described above; wherein R is a carboxy protecting group and R₅ is (a) hydrogen, C₁–C₄ alkyl or halo(C₁–C₄ alkyl);

(b) a group R₆ wherein R₆ is phenyl or phenyl substituted by 1 or 2 groups selected from the group consisting of fluoro, chloro, bromo, iodo, nitro, cyano, C₁–C₄ alkyl, C₁–C₄ alkoxy, protected hydroxy, carbamyl, trifluoromethyl and methanesulfonamido;

(c) a group of the formula

R₆(O)ₘCH₂— wherein m is 1 or 0 and R₆ is as defined above;

(d) a group of the formula

R₆ₐCH₂— wherein R₆ₐ is cyclohexadienyl, 2-furyl, 2-thienyl, or 3-thienyl; or (e) a group of the formula —COOR wherein R is as defined above.

Both cis and trans (halo with respect to carboxy) vinyl chloride products are produced in accordance with the present thiazoline enol halogenation process. The ratio of cis and trans products varies from substrate to substrate. For example, when R₅ is phenoxymethyl, X is chloro and R is 4-nitrobenzyl the ratio of cis and trans vinyl chloride products is about 1:1; however when R₅ is benzyl and X is chloro the cis isomer is the major product. The isomers can be separated by conventional chromatographic procedures.

Exemplary of the R₅ groups in accordance with the above definition are hydrogen, methyl, ethyl, sec-butyl, tert-butyl, chloromethyl, bromomethyl, 2-iodoethyl, 2-fluoropropyl, phenyl, 2-bromophenyl, 4-chlorophenyl, 4-methoxyphenyl, p-tolyl, o-tolyl, 4-benzyloxyphenyl, 3-carbamylphenyl, 4-chloro-3-cyanophenyl, 4-methoxy-2-tolyl, 4-trifluoromethylphenyl, benzyl, 4-methoxybenzyl, 4-iodobenzyl, 3-methanesulfonamidobenzyl, 3-nitrobenzyl, 3-chloro-4-benzyloxybenzyl, 2-ethylbenzyl, phenoxymethyl, 4-bromophenoxymethyl, 2-methoxyphenoxymethyl, 4-tolyloxymethyl, 4-chlorophenoxymethyl, 4-carbamylphenoxymethyl, 3-chloro-4-ethoxyphenoxymethyl and like groups. R₅ can also be 2-furylmethyl, 2-thienylmethyl, 3-thienylmethyl, cyclohexadienylmethyl, carbomethoxy, 4-nitrobenzyloxycarbonyl, 4-methoxybenzyoxycarbonyl, tertbutoxycarbonyl, benzhydryloxycarbonyl and the like.

The carboxylic acid protecting group (R) can be removed from the above-described thiazoline acetidinone vinyl halides by conventional procedures to provide the novel corresponding carboxylic acid derivatives of the formula

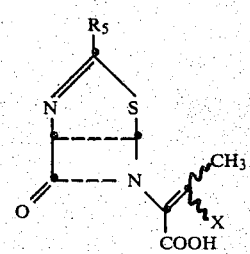

which compounds and their alkali metal salts exhibit activity against a number microorganisms, including *B. sublilis, Sarcina lutea, E. coli* and *Candicta albicans* among others. Accordingly these compounds find utility and a number of antibiotic applications. For example, they may be employed in aqueous compositions in concentrations of ranging from 100 to 1000 parts per million parts of solution, alone, or in conjunction with other antibiotic compounds to destroy and inhibit the growth of harmful bacteria on, for example, medicinal and dental equipment and as bactericides in industrial applications. Alternatively these compounds may be used alone or in combination with other antibiotics in any one of a number of pharmaceutical applications. These antibiotics and their alkali metal salts may be employed for human or veterinary use in capsule form or as tablets, powders or liquid solutions, or as suspensions or elixirs. They may be administered orally, intravenously or intramuscularly.

Each of the foregoing process embodiments of this invention can be described generally, and is referred to hereinafter, as enol-halogenations. It is preferred that each of the enol-halogenation processes described above be conducted in the presence of a tertiary amine base. Typically from about 1.0 to about 1.2 equivalents and preferably about 1.0 equivalents of a tertiary amine base is employed for each equivalent of halogenating agent used in the enol-halogenation process. Preferred tertiary amines bases for this process and the combination enol-halogenation/imino-halogenation described herein below are those having a pK$_b$ value of about 1 to about 10. More preferred are those tertiary amine bases having a pK$_b$ value of about 6 to about 10. Exemplary of suitable tertiary amine bases for use in the presence invention are trialkylamines such as trimethylamine, triethylamine, tri-n-propylamine, ethyldimethylamine, benzyldiethylamine and the like; dialkylarylamines such as dimethylaniline, diethylaniline, N,N-diethyl-4-methylaniline, N-methyl-N-ethylaniline, N,N-dimethyltoluidine and the like; cyclic and bicyclic tertiary amines such as pyridine, collidine, quinoline, isoquinoline, 2,6-lutidine, 2,4-lutidine, 1,5-diazabicyclo[4.3.0]nonene-5 (DBN), 1,5-diazabicyclo[5.4.0]undecene-5 (DBU), triethylenediamine and the like; and polymeric tertiary amine bases such as the copolymer formed from divinylbenzene and vinylpyridine described by Hallensleben and Wurm in *Angew. Chem. Intl. Ed. Engl.*, 15, 163 (1976). Pyridine is a preferred tertiary amine base.

In addition to the enol-halogenations described hereinabove the aforedescribed halogenating compounds can be employed advantageously in a process directed to a combination enol-halogenation/imino-halogenation of 7-acylamino-3-hydroxycephem to the corresponding 3-halocephem iminohalide compounds. In particular, this further embodiment of the present invention is directed to the process for preparing an imino halide compound of the formula

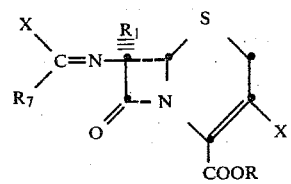

which comprises reacting a compound of the formula

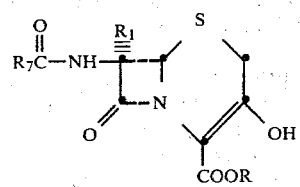

with about 2.0 to about 3.0 equivalents of a halogenating compound of the formula

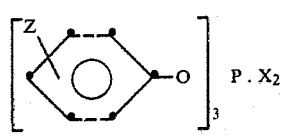

described in detail hereinabove, in the presence of about 1.0 to about 1.2 equivalents of a tertiary amine base per equivalent of halogenating compound employed, in a substantially anhydrous inert organic solvent at a temperature below about 30° C. wherein in the above formulas X is Cl or Br;
Z is hydrogen, halo, $C_1$–$C_4$ alkyl or $C_1$–$C_4$ alkoxy;
R is a carboxylic acid protecting group;
$R_1$ is hydrogen or methoxy;

and $R_7$ is the residue of an acyl group derived from a carboxylic acid of the formula $R_7$COOH; provided that when $R_7$ is substituted by amino, hydroxy or carboxy groups, those groups are first protected by one of the conventional amino, hydroxy, or carboxy protecting groups.

In the foregoing description of the process embodiments of the present invention the nitrogen containing C-7 substituent on the cephem substrates is defined in general terms as amido groups of the formula $R_3$NH— or $R_7$CONH— wherein $R_3$ and $R_7$CO are both acyl groups derived from carboxylic acids. Additionally in the case of the enol-halogenation process the C-7 group can be an acylic imido group of the formula $R_2R_3$N— wherein $R_2$ and $R_3$ are acyl groups derived from carboxylic acids or a cyclic imido group of the formula

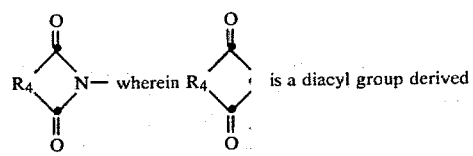

is a diacyl group derived from a dicarboxylic acid. Within this definition of the C-7 substituents the nature of the carboxylic acids from which these groups are derived is not critical to the present processes. The carboxylic acids from which the C-7 substituents are derived are typically $C_1$–$C_{20}$ carboxylic acids. A preferred group of C-7 acylamino substituents for the starting materials for the processes of the present invention are those conventional in the penicillin and cephalosporin art and includes but are not limited to those described in U.S. Pat. Nos. 3,947,413; 3,932,465; 3,954,732; 3,660,396; 3,948,927; 4,052,387; 4,053,469; 4,058,610; 4,066,641 and 4,042,585. Because of the reactivity of the halogenating agent of the present invention with protic functional groups, for example carboxy, amino and hydroxy groups, such functional groups if present on the C-7 side chain moiety of the 3-hydroxy-3-cephem substrate should first be protected using conventional carboxy, amino and hydroxy protecting groups. A non-limiting representation of C-7 acylamino groups for the substrate 3-hydroxy-3-cephems ($R_3$=$R_7$CO—) for the present processes are acylamino groups of the formula $R_7$CONH— wherein $R_7$ is (1) hydrogen, $C_1$–$C_4$ alkyl, halo($C_1$–$C_4$)-alkyl, cyanomethyl, trifluoromethylthiomethyl, or 4-protected amino-4-protected carboxybutyl;

(2) the group $R_a$ wherein $R_a$ is phenyl or phenyl substituted with 1 or 2 substituents selected from the group consisting of $C_1$-$C_4$ alkyl, $C_1$-$C_4$ alkoxy, protected hydroxy, chloro, bromo, fluoro, iodo, nitro, cyano, carbamyl, methanesulfonamido and trifluoromethyl;

(3) an arylalkyl group of the formula $$R^o-(Q)_m-CQ_1Q_2-$$

wherein $R^o$ is $R_a$ as defined above, 1,4-cyclohexadienyl, or a 5-membered heterocyclic ring containing 1 to 4 heteroatoms selected from the group consisting of oxygen, nitrogen, and sulfur, said ring being unsubstituted or substituted by $C_1$-$C_4$ alkyl, $C_1$-$C_4$ alkoxy, chloro, bromo, oxo, protected amino, protected amino($C_1$-$C_4$ alkyl), protected hydroxy or protected carboxy;

m is 1 or 0;

Q is oxygen or sulfur, and $Q_1$ and $Q_2$ are independently hydrogen or methyl; subject to the limitation that in the above formula when m is 1, $R^o$ is limited to $R_a$;

(4) a substituted arylalkyl group of the formula $$\begin{array}{c} R^oCH- \\ | \\ W \end{array}$$

wherein $R^o$ is as defined above and W is ureido, protected amino, protected hydroxy or protected carboxy; or (5) a substituted oximino group of the formula $$\begin{array}{c} R^O-C- \\ \| \\ NR_b \end{array}$$

wherein $R^o$ is defined as in paragraph (3) immediately hereinabove and $R_b$ is $C_1$-$C_4$ alkyl.

Exemplary of such acylamino groups are formamido, acetamido, propionamido, butyramido, chloroacetamido, 2-bromopropionamido, cyanoacetamido, trifluoromethylthioacetamido, 4-tert-butoxycarbonylamino-4-tert-butoxycarbonylbutyramido, benzamido, 4-methylbenzamido, 3-nitrobenzamido, 2-iodobenzamido, 4-benzyloxybenzamido, 3-cyanobenzamido, 2,6-dichlorobenzamido, 4-trifluoromethylbenzamido, 3,4-diethoxybenzamido, and 3-methanesulfonamidobenzamido.

When $R_7$ is a group $R^o-(Q)_m-CQ_1Q_2-$ representative acylamino groups are phenylacetamido, 4-bromophenylacetamido, 3,5-dinitrophenylacetamido, 4-benzyloxyphenylacetamido, phenoxyacetamido, 4-chlorophenoxyacetamido, 2-propoxyphenoxyacetamido, 4-carbamylphenoxyacetamido, cyclohexadienylacetamido, phenylthioacetamido, 2,5-dichlorophenylthioacetamido, 3-nitrophenylthioacetamido, 2-trifluoromethylphenylthioacetamido, 2-phenylpropionamido, 2-phenoxypropionamido, 2-phenyl-2-methylpropionamido, 2-(4-chlorophenyl)propionamido, 2-furylacetamido, 2-thienylacetamido, 5-isoxazolylacetamido, 2-thiazolylacetamido, 2-thienylpropionamido, 5-thiazolylacetamido, 2-chloroacetamidothiazol-5-ylacetamido, 5-bromothien-2-ylacetamido, 1-tetrazolylacetamido, 5-tetrazolylacetamido and the like.

Illustrative of the acylamino groups when $R_7$ is a substituted arylalkyl group of the formula $$\begin{array}{c} R^oCH- \\ | \\ W \end{array}$$

and when W is protected hydroxy are 2-formyloxy-2-phenylacetamido, 2-benzyloxy-2-(4-methoxyphenyl)acetamido, 2-(4-nitrobenzyloxy)-2-(3-chlorophenyl)acetamido, 2-chloroacetoxy-2-(4-methoxyphenyl)acetamido, 2-benzyloxy-2-phenylacetamido, 2-trimethylsilyloxy-2-(4-chlorophenyl)acetamido, 2-benzhydryloxy-2-phenylacetamido and like groups. Representative of such groups when W is protected amino are 2-(4-nitrobenzyloxycarbonylamino)-2-phenylacetamido, 2-(2,2,2-trichloroethoxycarbonylamino)-2-phenylacetamido, 2-chloroacetamido-2-(1,4-cyclohexadien-1-yl)acetamido, 2-(4-methoxybenzyloxycarbonylamino)-2-(4-methoxyphenyl)acetamido, 2-benzhydryloxycarbonylamino-2-phenylacetamido, 2-(1-carbomethoxy-2-propenyl)amino-2-phenylacetamido, 2-(4-nitrobenzyloxycarbonylamino)-2-(2-thienyl)-acetamido and like groups.

When W is protected carboxy the group $R_7COHN-$ can be 2-(4-nitrobenzyloxycarbonyl)-2-(2-thienyl)acetamido, 2-benzhydryloxycarbonyl-2-phenylacetamido, 2-(2,2,2-trichloroethoxycarbonyl)-2-(4-chlorophenyl)acetamido, 2-tert-butoxycarbonyl-2-(4-benzyloxyphenyl)acetamido and like groups.

Imido group represented by the formula

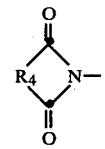

are maleimido, 3-ethylmaleimido, 3,4-dimethylmaleimido, succinimido, phthalimido, and 3,4,5,6-tetrahydrophthalimido.

The term "protected amino" as employed in the above definition has reference to an amino group substituted with one of the commonly employed amino blocking groups such as the tert-butoxycarbonyl group (t-BOC); the benzyloxycarbonyl group, the 4-methoxybenzyloxycarbonyl group, the 4-nitrobenzyloxycarbonyl group, the 2,2,2-trichloroethoxycarbonyl group, or the 1-carbomethoxy-2-propenyl group formed with methyl acetoacetate. Like amino protecting groups such as those described by J. W. Barton in *Protective Groups in Organic Chemistry*, J. F. W. McOmie, Ed., Plenum Press, New York, N.Y., 1973, Chapter 2, shall be recognized as suitable. Conventional amino protecting groups that form a —CONH— function with the protected amino group can be chlorinated under the conditions of the present process and subsequently removed. If such reaction is desired, it can be accomplished by adding an additional equivalent of halogenating reagent and an alcohol to cleave the resulting imino halide.

The term "protected hydroxy" has reference to the readily cleavable groups formed with an hydroxyl group such as the formyloxy group, the chloroacetoxy group, the benzyloxy group, the benzhydryloxy group, the trityloxy group, the 4-nitrobenzyloxy group, the trimethylsilyloxy group, the phenacyloxy group, the tert-butoxy group, the methoxymethoxy group, the tetrahydropyranyloxy group, and the like. Other hydroxy protecting groups, including those described by C. B. Reese in *Protective Groups in Organic Chemistry*, supra, Chapter 3 shall be considered as within the term "protected hydroxy" as used herein.

The term "carboxylic acid protecting group" has reference to the commonly used carboxylic acid protecting groups employed to block or protect the carboxylic acid functionality while reactions involving other functional sites of the compound are carried out. Such carboxy protecting groups are noted for their ease of cleavage by hydrolytic or by hydrogenolytic methods to the corresponding carboxylic acid. Examples of carboxylic acid ester protecting groups include methyl, tert-butyl, benzyl, 4-methoxybenzyl, $C_2$–$C_6$ alkanoyloxymethyl, 2-iodoethyl, 4-nitrobenzyl, diphenylmethyl (benzhydryl), phenacyl, 4-halophenacyl, dimethylallyl, 2,2,2-trichloroethyl, tri($C_1$–$C_3$ alkyl)silyl, succinimidomethyl and like ester forming moieties. In addition to ester protection of carboxy groups, such groups can also be protected as the mixed anhydride, such as that formed with acetyl chloride, propionyl chloride, isobutyryl chloride and like acid chlorides in the presence of a tertiary amine base. Other known carboxy protecting groups such as those described by E. Haslam in *Protective Groups in Organic Chemistry*, supra, Chapter 5, shall be recognized as suitable. The nature of such ester forming groups is not critical.

In the foregoing definitions hydroxy, amino and carboxy protecting groups are not exhaustively defined. The function of such groups is to protect the reactive functional groups during the present process and then to be removed at some later point in time without disrupting the remainder of the molecule. Many protecting groups are known in the art, and the use of other protecting groups not specifically referred to hereinabove are equally applicable to the substrates used in the processes of the present invention.

Although trace amounts of imino halide products have been noted in the enol-halogenation reactions first described above, carried out without base, the presence of a base appears to be required for effective imino chloride formation. Suitable bases are those tertiary amine bases described and exemplified hereinabove. As in the case of the enolhalogenation reaction, pyridine is a preferred tertiary amine base for the combination enolhalogenation/imino-halogenation process of the present invention. Typically about 1.0 to about 1.2 and preferably about 1 equivalent of tertiary amine base is employed for each equivalent of halogenating agent in the process.

The triphenyl phosphite-halogen complexes (Z=H) are the preferred halogenating agents in the halogenation processes of this invention. The triphenyl phosphite-chlorine kinetic complex is most preferred for the present processes. For the enol-halogenation process, best results are seen when about 1.1 to about 1.2 equivalent of halogenating reagent are used for each equivalent of enol substrate. For the combination enol-halogenation/imino-halogenation process, preferably about 2.2 to about 2.4 equivalents, and most preferably about 2.3 equivalents, of halogenating compounds are employed for each equivalent of enol substrate.

The halogenation processes of this invention are preferably carried out at a temperature of about 0° or below. A reaction temperature of about −10° or below is more preferred. Usually the prsent processes are not conducted at a temperature below about −70° C. Most preferred is a reaction temperature of about −10° to about −70° C. It should be noted that the present chlorination processes can be conducted, although not advantageously, at temperatures above 30° and below −70°. The freezing point of the reaction medium and substrate solubility are limiting factors at low temperatures while the ability of the thermodynamically unstable halogenating agent is the main consideration in selection of higher reaction temperatures. Of course, if the halogenating agent has been stabilized in solution with a tertiary amine base as described hereinabove, the upper temperature range for the present process becomes even a less critical variable; higher temperatures could easily be employed without significant loss of the halogenating agent and without detriment to the halogenation process itself.

Solvents which may be employed are the same as those described hereinabove for the preparation of the triaryl phosphite-halogen kinetic complexes. Preferred solvents are aromatic hydrocarbons of halogenated hydrocarbons.

The enol starting materials for the halogenation processes of the present invention are known compounds or can be easily derived from known compounds by conventional procedures. The 7-acylamino-3-hydroxy-3-cephems are described, for example, in U.S. Pat. Nos. 3,917,587 and 3,917,588, both issued November 4, 1975. They are derived generally by ozonylsis of the corresponding known 7-acylamino-3-methylenecephams. The thiazolineazetidinone enols of the formula

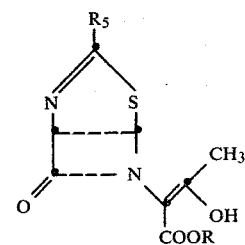

are prepared by mild ozonolysis of the corresponding compounds of the formula

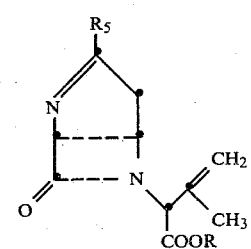

described in U.S. Pat. No. 3,705,892 issued Dec. 12, 1972. The thiazoline azetidinone enols are described as intermediates to 3-hydroxycephems in U.S. Pat. No. 4,079,181 issued Mar. 14, 1978.

The 7-acylamino 3-halocephem and thiazolineazetidinone vinyl halide products from the enol-halogenation processes of the present invention can be isolated and purified by conventional-laboratory techniques including for example extraction, crystallization and recrystalization, trituration and chromatography.

The 3-halocephem imino halide products of the combination enol-halogenation/imino-halogenation process of this invention can likewise be isolated using conventional laboratory techniques. However, because these products are sensitive to acid catalyzed alcoholysis or hydrolysis and to nucleophilic attack, some precaution should be taken during product isolation to avoid exposing the products to conditions under which such reactions of the imino halide might take place. Since the primary utility of a 3-halocephem imino halide is as an intermediate to the corresponding 3-halo cephem nucleus (7-amino) compounds, preferably the 3-halocephem imino halide product is reacted without isolation from the halogenating reaction mixture with an excess of a $C_1-C_{15}$ aliphatic alcohol or more preferably a β-disubstituted primary aliphatic alcohol or a 1,2- or 1,3-diol to provide the corresponding 3-halocephem nucleus esters of the formula

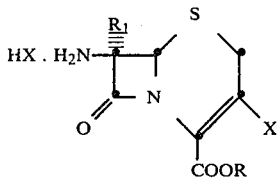

The alcoholysis of cephem imino halides via an imino ether intermediate using β-disubstituted aliphatic alcohols and 1,2 or 1,3-diols to provide cephem nucleus esters is disclosed in U.S. Pat. No. 3,845,043, issued Oct. 29, 1974, and U.S. Pat. No. 3,868,368 issued Feb. 25, 1975 respectively.

Preferred for alcoholysis of the present imino halide are a $C_4-C_{12}$ β-disubstituted primary aliphatic alcohol, a $C_3-C_{15}$ aliphatic 1,3-diol, or a $C_2-C_{12}$ aliphatic 1,2-diol. Suitable β-disubstituted primary aliphatic alcohols are those compounds of the formula

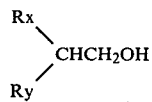

wherein each of $R_x$ and $R_y$ is an alkyl group such that the β-disubstituted primary aliphatic alcohol has from 4 to about 12 carbon atoms, or $R_x$ and $R_y$ are taken together with the carbon atom to which they are bonded to form a cycloalkyl group having from 5 to 8 carbon atoms. Exemplary of such alcohols are isobutanol, 2-methylbutanol, 2-ethylbutanol, 2-ethylhexanol, hydroxymethylcyclopentane, hydroxymethylcyclohexane, 2-n-butyloctanol, 2-n-propylhexanol and like alcohols. Suitable 1,2- or 1,3-diols are those of the formula

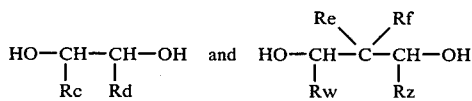

respectively wherein $R_c$ and $R_d$ is hydrogen or alkyl such that the 1,2-diol has from 2 to 12 carbon atoms and wherein $R_w$ and $R_z$ is each hydrogen, methyl or ethyl, and each of $R_e$ and $R_f$ is hydrogen or a hydrocarbon moiety such that the 1,3-diol has from 3 to 15 carbon atoms. Representative of 1,2-diols are 1,2-propylene glycol, 2,3-butanediol, 1,2-butanediol, 3,4-pentanediol and 3,4-hexanediol. Representative of 1,3-diols are 1,3-propanediol, 1,3-butanediol, 1,3-pentanediol, 2,2-dimethyl-1,3-propanediol, 2,2-diethyl-1,3-propanediol, 2,4-pentanediol and 2,2-diphenyl-1,3-propanediol. Most preferred of alcohols or diols for cleavage of the 3-halocephem imino halide products of the present process are isobutanol, 1,2-propanediol and 1,3-propanediol.

An excess of the alcohol or diol is employed for alcoholysis of the 3-halocephem imino halides provided by the present halogenation process. The amount of excess alcohol or diol is not critical. When the aforedescribed 1,2- or 1,3-diols are used, about a 2–3 fold excess will suffice. When a β-disubstituted primary aliphatic alcohol is employed, about a 3–6 fold excess is usually preferred. Of course larger amounts of the alcohol or diol may be employed without affecting the course of the reaction. Often a 3–15 fold excess is employed. When aliphatic alcohols other than those mentioned hereinabove as preferred are used to cleave the imino halide products of the present process, larger excesses, 10–100 fold, have typically been employed. Usually the alcohol or diol is simply added to the halogenating reaction mixture in which the 3-halocephem imino halide has been prepared in accordance with the process of the present invention.

Alcholysis of the imino chloride (via imino ether formation) is acid catalyzed. The chlorinating reaction mixture is usually acidic enough so that alcoholysis occurs upon alcohol or diol addition without the addition of acid to the reaction mixture. However, to enhance the rate of alcoholysis and therefore the rate of nucleus ester formation, the reaction mixture is preferably acidified with, for example, hydrogen chloride after the alcohol or diol has been added to the reaction mixture. This can be accomplished simply by bubbling HCl gas into the reaction mixture for a short period of time. Typically about 1 equivalent of hydrogen chloride is added to the reaction mixture to promote nucleus ester formation.

Combining the aforedescribed enol-halogenation-/imino-halogenation process, where X is Cl, with subsequent alcoholysis of the resulting imino chloride constitutes an improved method of preparation of 7-amino-3-chloro-3-cephem-4-carboxylic acid esters from the corresponding 7-acylamino-3-hydroxy-3-cephem-4-carboxylic acid esters. Prior to this invention the total conversion was effected by first converting a 7-acylamino-3-hydroxy-3-cephem substrate to the corresponding 7-acylamino-3-chloro-3-cephem and then cleaving the side chain of that compound in accordance with art recognized procedures. With the discovery of the novel triaryl phosphite-chlorine complex and the present processes utilitizing that reagent, the chlorination-cleavage conversion can be effected in one reaction vessel without isolation of the 7-acylamino-3-chloro-3-cephem intermediate.

The product nucleus ester can be isolated as its crystalline hydrochloride, in the case of the p-nitrobenzyl ester, by simply filtering the crystallized product from the reaction mixture. Non-crystalline 3-chlorocephem nucleus esters produced in accordance with the foregoing procedure can be isolated from the reaction mixture using conventional laboratory techniques. Alternatively the nucleus esters can be reacted (acylated) in solution without being isolated.

The 3-halocephem nucleus esters are known compounds. They can be acylated using conventional acylation techniques and subsequently deesterified to provide known antibiotic 7-acylamino-3-chloro or bromo-3-cephem-4-carboxylic acids. Of particular significance is the utility of these nucleus ester intermediates in the preparation of 7-(D-2-phenyl-2-aminoacetamido)-3-chloro-3-cephem-4-carboxylic acid a relatively new and clinically significant antibiotic.

In a preferred process embodiment of the present invention a 7-amino-3-chloro-3-cephem-4-carboxylic acid ester hydrochloride of the formula

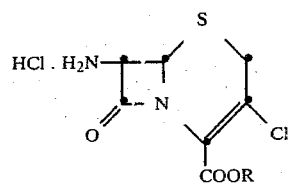

is prepared by (a) reacting a 7-acylamino-3-hydroxy-3-cephem-4-carboxylic acid ester with about 2.3 equivalents of the kinetically controlled product of the reaction of equivalent amounts of triphenyl phosphite and chlorine in a substantially anhydrous inert organic solvent, in the presence of about 2.3 equivalents of pyridine in a substantially anhydrous inert organic solvent, at a temperature of about −10° to about −30° C.;

(b) adding about 3 to about 15 equivalents of isobutanol, 1,3-propanediol or 1,2-propanediol to the reaction mixture after formation of the 3-chloro-3-cephem imino chloride is complete; and (c) acidifying the reaction mixture with HCl.

Preferred inert organic solvents are aromatic hydrocarbon or halogenated hydrocarbon solvents.

Preferred 3-hydroxy-3-cephem substrates are those bearing conventional penicillin and cephalosporin carboxamido groups at the C-7 position. Preferred for economic reasons and not necessarily for reactivity are the C-7 substituents phenylacetamido, phenoxyacetamido and 2-thienylacetamido. Similarly the 4-nitrobenzyl group is a preferred carboxy protecting group in this preferred process embodiment because of the crystalline nature of the product hydrochloride, and therefore the ease of isolation of a product nucleus ester of high purity.

The following examples are provided to further illustrate the present invention. It is not intended that this invention be limited in scope by reason of any of these examples. In the following examples and preparations nuclear magnetic resonance spectra are abbreviated nmr. The chemical shifts are expressed in δ values in parts per million (ppm) and coupling constants (J) are expressed in Hz (cycles per second).

EXAMPLE 1

4'-Nitrobenzyl 7-phenylacetamido-3-chloro-3-cephem-4-carboxylate.

Chlorine was bubbled through a solution of 2.89 ml (11 mmol) of triphenyl phosphite in 50 ml of methylene chloride at −15° C. until the yellow color indicative of excess chlorine persisted. The color was then discharged by the addition of 2 drops of triphenyl phosphite. To the resulting solution of the triphenyl phosphite-chlorine reagent were added 4.54 gm (10 mmol) of 4'-nitrobenzyl 7-phenylacetamido-3-hydroxy-3-cephem-4-carboxylate and, dropwise over a 40 minute period, a solution of 0.89 ml (11 mmol) of pyridine in 8 ml of methylene chloride. During the pyridine solution addition the temperature of the reaction mixture was maintained at −15° to −10° C. The reaction mixture was then stirred at −15° to −10° C. for an additional 60 minutes after which time the reaction mixture was removed from the cooling bath. Then 1 ml of conc. HCl was added to the mixture to effect hydrolysis of the small amount of imino chloride which had been formed. After stirring the reaction mixture for 30 minutes at room temperature the mixture was diluted with 100 ml of 3A ethanol, stirred 15 minutes, and then filtered to provide 2.67 grams (54.7%) of the title product as white crystals: m.p. 214° C. (decomp.). A second crop of the title product was obtained by concentrating the filtrate under a reduced pressure to a volume of about 50 ml An additional 1.52 grams (31.1%) of the title product was isolated. Total yield: 85.8%.

nmr (DMSO d-6) δ 3.62 (s, 2), 3.94 (ABq, 2, J=18 Hz), 5.3 (d, 1, J=5 Hz), 5.52 (s, 2), 5.82 (q, 1, J=5 and 8 Hz) and 7.2–8.4 (ArH).

Anal calcd for $C_{22}H_{18}N_3O_6SCl$: C, 54.16; H, 3.72; N, 8.61; Cl, 7.27; S, 6.57. Found: C, 53.91; H, 3.92; N, 8.44; Cl, 7.27; S, 6.55.

EXAMPLE 2

4'-Nitrobenzyl 7-phenoxyacetamido-3-chloro-3-cephem-4-carboxylate.

Following the procedure of Example 1 the triphenyl phosphite-chlorine kinetic product was prepared from 6.31 ml of triphenyl phosphite and chlorine in 45 ml of methylene chloride at −15° C. To this solution at −15° to −10° C. 5.24 gm (10 mmol) of 4'-nitrobenzyl 7-phenoxyacetamido-3-hydroxy-3-cephem-4-carboxylate was added and washed into the reaction mixture with 5 ml of methylene chloride. Then 1.01 ml (12.5 mmol) of pyridine in 8 ml of methylene chloride was added dropwise to the solution over a 30 minutes period. After stirring the reaction mixture for 2 hours at −10° C. 1 ml of conc. HCl was added. After stirring an additional 30 minutes the reaction mixture was washed with three 100 ml-portions of water, dried over magnesium sulfate, and evaporated in vacuo to an oil which was subsequently crystallized from 100 ml of 2B ethanol to provide 4.19 grams (83.2%) of the title product: m.p. 142.5°–146° C.

nmr (CDCl₃) δ 3.7 (ABq, 2, J=18 Hz), 4.60 (s, 2), 5.12 (d, 1, J=5 Hz), 5.4 (s, 2), 5.93 (q, 1, J=5 and 9 Hz), and 6.8–8.4 (ArH).

Anal calcd for $C_{22}H_{18}N_3O_7SCl$: C, 52.44; H, 3.60; N, 8.34; S, 6.36; Cl, 7.04. Found: C, 52.67; H, 3.73; N, 8.12; S, 6.15; Cl, 6.95.

EXAMPLE 3

4'-Nitrobenzyl 7-phenoxyacetamido-3-chloro-3-cephem-4-carboxylate using tri(o-tolyl)phosphite-chlorine complex.

Chlorine gas was bubbled into a solution of 3.91 gm (10 mmol) of tri(o-tolyl)phosphite in 45 ml of methylene chloride at −10° C. until a yellow color persisted. The color was then discharged by the addition of approximately 0.5 mmol of the phosphite. To the resulting solution at −10° C. was added 5.4 gm (10 mmol) of 4'-nitrobenzyl 7-phenoxyacetamido-3-hydroxy-3-cephem-4-carboxylate which was washed into the solution with 5 ml of methylene chloride. Then 1.01 ml (12.5 mmol) of pyridine was added. After allowing the reaction mixture to stir for 90 minutes at −10° C., 1 ml of conc. HCl was added to the reaction mixture. After stirring for an additional 30 minutes the reaction mixture was washed successively with two 25 ml-portions of water and 25 ml of dilute sodium chloride solution, dried over sodium sulfate, and evaporated in vacuo to an oil which crystallized from 50 ml of 2B ethanol to provide 3.35 grams (66.5%) of the title product. An nmr spectrum of the product was identical to that of the product obtained in Example 2.

EXAMPLE 4

4'-Nitrobenzyl 7-phenoxyacetamido-3-chloro-3-cephem-4-carboxylate.

(A) Clorination without base.

A solution of the triphenyl phosphite-chlorine reagent was prepared as described in Example 1 above from 2.89 ml of triphenyl phosphite in methylene chloride at −10° C. To this solution was added 4.86 gm (10 mmol) of 4'-nitrobenzyl 7-phenoxyacetamido-3-hydroxy-3-cephem-4-carboxylate. The reaction mixture was stirred at −10° C. for 2 hours. Comparative thin layer chromatography showed that the chlorination after about 2 hours was approximately 50% complete; some imino chloride was also noted.

(B) 2,6-Lutidine.

To the reaction mixture described in Paragraph A immediately above was added 1.2 ml (10.5 mmol) of 2,6-lutidine. After stirring the reaction mixture at −10° C. for 60 minutes 1 ml of conc. HCl was added. The reaction mixture was then removed from the cooling bath and stirred an additional 30 minutes after which time it was washed successively with two 100 ml-portions of water and 100 ml of dilute sodium chloride solution. The reaction mixture was then dried over magnesium sulfate and evaporated in vacuo to an oil which crystallized from 75 ml of 2B ethanol to provide 3.83 grams (76%) of the title product: m.p. 124°–126° C.

EXAMPLE 5

4'-Nitrobenzyl α-[3-phenoxymethyl-7-oxo-2,6-diaza-4-thiabicyclo[3.2.0]hept-2-en-6-yl]-α-(1-chloroethylidene)acetate.

To a solution of chlorine in a mixture of 16 ml of carbon tetrachloride and 20 ml of methylene dichloride at −10° C. was added 3.14 ml (12 mmol) of triphenyl phosphite at such a rate that the temperature did not rise above −5° C. until a colorless endpoint was reached. After cooling the reaction mixture to 10° C. 2.54 gm (5.41 mmol) of 4'-nitrobenzyl α-[3-phenoxymethyl-7-oxo-2,6-diaza-4-thiabicylco-[3.2.0]hept-2-en-6-yl]-α-(1-hydroxyethylidene)acetate was added. After most of the substrate had dissolved in the reaction mixture, 1.45 ml (13 mmol) of pyridine in 10 ml of methylene chloride was added over a 50 minute period. Following the pyridine addition the reaction mixture was removed from the cooling bath and stirred at room temperature for about 70 minutes. After this time the reaction mixture was diluted with ethyl acetate and washed successively with two 50 ml-portions of 1 N. HCl, 50 ml of saturated sodium bicarbonate solution, and 100 ml of saturated sodium chloride solution. The organic layer was dried over magnesium sulfate and evaporated in vacuo to dryness to provide about 1.4 grams of the title product as a mixture of the cis and trans chloro isomers. The isomers were separated by chromatography over 40 grams of silica gel using 10% ethyl acetate/toluene as the eluent.

First isomer off column: nmr (CDCl$_3$) δ 2.63 (s, 3), 4.65 (ABq, 2), 5.2 (s, 2), 6.01 (s, 2, β-lactam H), and 6.7–8.3 (ArH).

Second isomer off column: nmr (CDCl$_3$) δ 2.16 (s, 3), 4.93 (s, 2), 5.33 (s, 2), 5.87 (s, 1, J=4 Hz), 6.1 (bd, 1, J=4 Hz) and 6.7–8.3 (ArH).

EXAMPLE 6

4'-Nitrobenzyl 7-amino-3-chloro-3-cephem-4-carboxylate, hydrochloride.

(A) Methylene chloride, pyridine.

Chlorine gas was bubbled into a soluton of 6.31 ml (25 mmol) of triphenyl phosphite in 45 ml of methylene chloride at −10° C. until the yellow color of excess chlorine persisted. The color was then discharged with the addition of several drops of triphenyl phosphite. To this solution of the triphenyl phosphite-chlorine reagent at −15° C. was added 4.86 gm (10 mmol) of 4'-nitrobenzyl 7-acetamido-3-hydroxy-3-cephem-4-carboxylate. Subsequently 2.02 ml (12.5 mmol) or pyridine in 8 ml of methylene chloride was added dropwise to the reaction mixture over a 40 minutes period. After stirring the reaction mixture for 30 minutes at −10° C., 9.25 ml (100 mmol) of isobutanol was added. The reaction mixture was then removed from the ice bath and treated with gaseous HCl for about 30 seconds. Although the product began to crystallized within 5 minutes, the reaction mixture was stirred at about 20 for 2 hours and then filtered to provide 3.33 grams (82%) of the titled nucleus ester hydrochloride: m.p. 181° C. (dec.).

nmr (DMSO d-6) δ 4.06 (bs, 2), 5.33 (q, 2, J=4.5 Hz, β-lactam H), 5.5 (s, 2), 7.8–8.3 (ArH) and ~8.6 (very broad s, —NH$_3^+$).

(B) 1,2-Dichloroethane, pyridine.

The same procedure was followed as described in Example 6A immediately above except that the solvent methylene chloride was replaced with 1,2-dichloroethane. A total of 3.10 grams (76.4%) of titled nucleus ester hydrochloride product was isolated.

(C) Methylene chloride, quinoline.

The same procedure was followed as described in Paragraph A above except the the pyridine base was replaced with quinoline. A total of 3.2 grams (79.8%) of the titled product was isolated: m.p. 181° C. (dec.).

(D) Methylene chloride, isoquinoline.

The same procedure was followed as described in Paragraph A above except that isoquinoline was employed in place of the pyridine base. The reaction mixture was notably darker than in previous experiments. A total of 2.29 grams (56.4%) of the title product was isolated: m.p. 181° C. (dec.).

(E) Methylene chloride, N,N-dimethylaniline.

The same procedure was followed as described in Paragraph A above however, N,N-dimethylaniline was employed at the base in place of pyridine. A total of 0.91 grams (22.4%) of the title product was isolated: m.p. 182° C. (dec.).

(F) Acetonitrile, pyridine.

Chlorine gas was bubbled into a mixture of 7.9 ml (30 mmol) of triphenyl phosphite in 45 ml of acetonitrile at −10° C. Because the mixture solidified it was allowed to warm to 10° C. whence the reaction mixture again liquified. The addition of chlorine gas was continued until a yellow color persisted in the mixture. Then 0.1 ml of triphenyl phosphite was added to decolorize th solution (about 30.4 mmol of the triphenyl phosphite-chlorine kinetic compound was formed). To this solution was added 5.4 gm (10 mmol) of 4'-nitrobenzyl 7-phenoxyacetamido-3-hydroxy-3-cephem-4-carboxylate.

Thereafter 2.42 ml (30 mmol) of pyridine in 8 ml of acetonitrile was added dropwise over a 30 minute period with the temperature of the reaction mixture at 0° to 10° C. After stirring the reaction mixture for 1 hour, the cooling bath was removed, and the reaction mixture was allowed to stir at room temperature for 90 minutes. Then 9.25 ml (100 mmol) of isobutanol was added. After 90 minutes at room temperature the reaction mixture was filtered to provide 0.95 gm (23.4%) of the titled nucleus ester hydrochloride: m.p. 186° C. (dec.).

(G) From 4'-Nitrobenzyl 7-phenylacetamido-3-hydroxy-3-cephem-4-carboxylate.

A solution of the triphenyl phosphite-chlorine kinetic compound was prepared in accordance with the procedure described in Paragraph 6A above using chlorine and 2.89 ml (11 mmol) of triphenyl phosphite in 45 ml of methylene chloride. To this solution was added 2.3 gm (5 mmol) of 4'-nitrobenzyl 7-phenylacetamido-3-hydroxy-3-cephem-4-carboxylate. Then a solution of 0.89 ml (11 mmol) of pyridine and 5 ml of methylene chloride was added dropwise with stirring at −15° to −10° C. over a 15 minutes interval. After the reaction mixture was stirred for 1.5 hours at −15° to −10° C., the cooling bath was removed, and 6 ml (64.8 mmol) of isobutanol was added. As the mixture was stirred for the next hour, the mixture warming to 23° C., the product crystallized from the reaction mixture. Filtration of the mixture provided 1.59 grams (78.3%) of the nucleus ester hydrochloride as white crystals: m.p. 188° C. (dec.).

(H) Using tri(o-tolyl)phosphite-chlorine kinetic complex.

Chlorine gas was bubbled into a solution of 9.24 gm (26 mmol) of tri(o-tolyl)phosphite in 45 ml of methylene chloride at −10° C. until a yellow color persisted. About 0.5 mmol of the phosphite was then added to the mixture to consume the excess chlorine. To the solution was added 5.44 gm (10 mmol) of 4'-nitrobenzyl 7-phenoxyacetamido-3-hydroxy-3-cephem-4-carboxylate which was washed into the reaction mixture with 5 ml of methylene chloride. A solution of 2.58 ml (32 mmol) of pyridine in 8 ml of methylene chloride was then added dropwise to the reaction mixture at −10° C. over a period of 30 minutes. After the reaction mixture was stirred for 30 minutes at −10° C., 9.25 ml (100 mmol) of isobutanol was added. The reaction mixture was then removed from the ice bath, and HCl gas was bubbled in for about 60 seconds. The reaction mixture was then allowed to stir at room temperature for 90 minutes after which time it was filtered to provide 3.31 gm (81.5%) of the title nucleus ester hydrochloride: m.p. 183° C. (dec.).

EXAMPLE 7

4'-Nitrobenzyl 7-(1-chloro-2-phenoxyethylidene)imino-3-chloro-3-cephem-4-carboxylate.

The same procedure was followed as described in Example 6A above except that instead of adding isobutanol to the reaction mixture 4.2 ml of propylene oxide was added. Thereafter the reaction mixture was allowed to stir for 15 minutes at 0° C. The reaction mixture was then washed with 50 ml of ice water and then dried over calcium chloride dihydrate. Evaporation in vacuo of the dried solution yielded 21 gm of the dark color syrup. The addition of diethyl ether (containing a few drops of propylene oxide) to the residue deposited a small amount of tar. Then 5 ml of methylene chloride was then added to the mixture, and the resulting solution was decanted from about 1 gm of a black tar. Evaporation in vacuo of the solution gave a syrup which was triturated under 50 ml of 1:1 ether/hexane and decanted, three times, which provided a semi solid which after being stored in a refrigerator for several days was triturated under ether to provide 1.08 gm of a solid identified by nmr as 4'-nitrobenzyl 7-phenoxyacetamido-3-chloro-3-cephem-4-carboxylate. Evaporation of the filtrate in vacuo provided a foam which was dissolved in a few ml of methylene chloride. The resulting solution was diluted with some ether and then with about 50 ml of 2B alcohol (containing a few drops of propylene oxide). The titled imino chloride (0.24 gm) crystallized (m.p. 97°–98° C.) from the solution. The structure of the product was confirmed by its nmr spectrum.

nmr (CDCl$_3$, pyridine d-5) δ 3.56 (ABq, 2, J=18 Hz), 4.8 (s, 2), 5.03 (d, 1, J=5 Hz), 5.3 (s, 2), 5.53 (d, 1, J=5 Hz) and 6.9–8.3 (ArH).

EXAMPLE 8

4'-Nitrobenzyl 7-amino-3-chloro-3-cephem-4-carboxylate, hydrochloride.

(A) A solution of about 25.5 mmole of the triphenyl phosphite-chlorine compound was prepared by bubbling chlorine gas into a solution of 6.31 ml (24 mmol) of triphenyl phosphite in 45 ml of methylene chloride at −10° C. until an excess of chlorine was noted. Additional triphenyl phosphite (about 1.5 mmol) was added to the solution to discharged the yellow color. To this solution was added 5.24 gm (10 mmol) of 4'-nitrobenzyl 7-phenoxyacetamido-3-hydroxy-3-cephem-4-carboxylate which was washed into the reaction mixture with an additional 5 ml of methylene chloride. Subsequently a solution of 2.02 ml of pyridine in 8 ml of methylene chloride was added dropwise over a period of 40 minutes. The temperature of the reaction mixture was maintained at −10° to −15° C. After the reaction mixture was stirred for 25 minutes at −10° to −15° C., 9.25 ml of isobutanol (100 mmol) was added to the reaction mixture. Immediately thereafter the reaction mixture was removed from the cooling bath, and gaseous HCl was bubbled into the mixture for about 30 seconds. The reaction mixture was then seeded and allowed to stir at 20° C. for about 2 hours. Filtration provided 3.49 gm (86%) of the titled nucleus hydrochloride as white crystals: m.p. 179°–180° C. (decomp.).

(B) Essentially the same procedure was followed as described in Paragraph A immediately hereinabove except that 3.61 ml of 1,3-propanediol was substituted for the isobutanol. A total 3.25 gm (80%) of the titled product was isolated: m.p. 182° C. (decomp.).

EXAMPLES 9–21

Following the general experimental procedure described in Example 1 the following conversions are carried out employing halogenating compounds derived from the indicated triaryl phosphite and halogen.

EXAMPLE 29

Phenacyl α-[3-(2-carbomethoxy)-7-oxo-2,6-diaza-4-thiabicyclo[3.2.0]hept-2-en-6-yl]-α-(1-chloroethylidene)acetate from phenacyl α-[3-(2-carbomethoxy)-7-oxo-2,6-diaza-4-thiabicyclo[3.2.0]hept-2-en-6-yl]-α-(1-hydroxyethylidene)-acetate; triphenyl phosphite.

EXAMPLE 30

4′-Nitrobenzyl α-[3-(2-thienylmethyl)-7-oxo-2,6-diaza-4-thiabicyclo[3.2.0]hept-2-en-6-yl]-α-(1-chloroethylidene)acetate from 4′-nitrobenzyl-α-[3-(2-thienylmethyl)-7-oxo-2,6-diaza-4-thiabicyclo[3.2.0]hept-2-en-6-yl]-α-(1-hydroxyethylidene)acetate; triphenyl phosphite.

EXAMPLE 31–39

Following the experimental procedure described in Example 6(A), 4′-nitrobenzyl 7-amino-3-chloro-3-cephem-4-carboxylate hydrochloride is prepared from the following named 3-hydroxycephems using the chlorinating agent derived from chlorine and the indicated triaryl phosphite.

EXAMPLE 31

4′-Nitrobenzyl 7-formamido-3-hydroxy-3-cephem-4-carboxylate; triphenyl phosphite.

EXAMPLE 32

4′-Nitrobenzyl 7-phenylacetamido-3-hydroxy-3-cephem-4-carboxylate; tri(o-tolyl)-phosphite.

EXAMPLE 33

4′-Nitrobenzyl 7-(2-thienylacetamido)-3-hydroxy-3-cephem-4-carboxylate; triphenyl phosphite.

EXAMPLE 34

4′-Nitrobenzyl 7-phenoxyacetamido-3-hydroxy-3-cephem-4-carboxylate; triphenyl phosphite.

EXAMPLE 35

4′-Nitrobenzyl 7-benzamido-3-hydroxy-3-cephem-4-carboxylate; triphenyl phosphite.

EXAMPLE 36

4′-Nitrobenzyl 7-phenylthioacetamido-3-hydroxy-3-cephem-4-carboxylate; tri(o-tolyl)-phosphite.

EXAMPLE 37

4′-Nitrobenzyl 7-[2-(tert-butoxycarbonylamino)-2-phenylacetamido]-3-hydroxy-3-cephem-4-carboxylate; triphenyl phosphite.

EXAMPLE 38

4′-Nitrobenzyl 7-phenoxyacetamido-3-hydroxy-3-cephem-4-carboxylate; tri(p-methoxyphenyl)phosphite.

EXAMPLE 39

4′-Nitrobenzyl 7-phenylacetamido-3-hydroxy-3-cephem-4-carboxylate; tri(p-tolyl)-phosphite.

EXAMPLES 40–47

Following the general experimental procedure described in Example 6A, the following conversions are carried out using the chlorinating compound derived from chlorine or bromine and the indicated triaryl phosphite.

EXAMPLE 40 tert-Butyl 7-amino-3-chloro-3-cephem-4-carboxylate from tert-butyl 7-phenylacetamido-3-hydroxy-3-cephem-4-carboxylate; triphenyl phosphite.

EXAMPLE 41

4′-Nitrobenzyl 7-methoxy-7-amino-3-chloro-3-cephem-4-carboxylate from 4′-Nitrobenzyl 7-methoxy-7-phenoxyacetamido-3-hydroxy-3-cephem-4-carboxylate; triphenyl phosphite.

EXAMPLE 42

2′,2′,2′-trichloroethyl 7-amino-3-bromo-3-cephem-4-carboxylate from 2′,2′,2′-trichloroethyl 7-acetamido-3-hydroxy-3-cephem-4-carboxylate; tri-o-tolyl phosphite.

EXAMPLE 43

Benzyl 7-amino-3-chloro-3-cephem-4-carboxylate from benzyl 7-(4-chlorophenoxyacetamido)-3-hydroxy-3-cephem-4-carboxylate; tri(p-ethoxyphenyl) phosphite.

EXAMPLE 44

Benzhydryl 7-methoxy-7-amino-3-chloro-3-cephem-4-carboxylate from benzhydryl 7-methoxy-7-phenylacetamido-3-hydroxy-3-cephem-4-carboxylate; triphenyl phosphite.

EXAMPLE 45

4′-Nitrobenzyl 7-amino-3-bromo-3-cephem-4-carboxylate from 4′-nitrobenzyl 7-(3-nitrobenzamido)-3-hydroxy-3-cephem-4-carboxylate; triphenyl phosphite.

EXAMPLE 46

4′-Methoxybenzyl 7-amino-3-chloro-3-cephem-4-carboxylate from 4′-methoxybenzyl 7-[2-formyloxy-2-phenylacetamido]-3-hydroxy-3-cephem-4-carboxylate; tri(m-tolyl) phosphite.

EXAMPLE 47

4-Nitrobenzyl 7-amino-3-bromo-3-cephem-4-carboxylate from 4′-nitrobenzyl 7-(2-thienylacetamido)-3-hydroxy-3-cephem-4-carboxylate; triphenyl phosphite.

EXAMPLE 48–55

Following the general experimental procedures described in Example 7, the following compound conversions are carried out using a chlorinating compound derived from chlorine or bromine and the indicated triaryl phosphite.

EXAMPLE 48

4′-Nitrobenzyl 7-methoxy-7-(α-chlorobenzylidene)imino-3-chloro-3-cephem-4-carboxylate from 4′-nitrobenzyl 7-methoxy-7-benzamido-3-hydroxy-3-cephem-4-carboxylate; triphenyl phosphite.

EXAMPLE 49

Benzyl 7-(1-chloro-2-phenylethylidene)-imino-3-chloro-3-cephem-4-carboxylate from benzyl 7-phenylacetamido-3-hydroxy-3-cephem-4-carboxylate; tri(o-tolyl) phosphite.

EXAMPLE 50

2′,2′,2′-trichloroethyl 7-[1-chloro-2-(2-thienyl)ethylidene)imino]-3-chloro-3-cephem-4-carboxylate from 2',2',2'-trichloroethyl-7-(2-thienylacetamido)-3-hydroxy-3-cephem-4-carboxylate; triphenyl phosphite.

EXAMPLE 51

4'-Methoxybenzyl 7-(1-chloroethylidene)-3-chloro-3-cephem-4-carboxylate from 4'-methoxybenzyl 7-acetamido-3-hydroxy-3-cephem-4-carboxylate; triphenyl phosphite.

EXAMPLE 52

4'-Nitrobenzyl 7-(1-bromo-2-phenoxyethylidene)imino-3-bromo-3-cephem-4-carboxylate from 4'-nitrobenzyl 7-phenoxyacetamido-3-hydroxy-3-cephem-4-carboxylate; triphenyl phosphite.

EXAMPLE 53 tert-Butyl 7-(1-chloro-2-chloroacetoxy-2-phenylethylidene)imino-3-chloro-3-cephem-4-carboxylate from tert-butyl 7-(2-chloroacetoxy-2-phenylacetamido)-3-hydroxy-3-cephem-4-carboxylate; tri(o-methoxyphenyl) phosphite.

EXAMPLE 54

4'-Nitrobenzyl 7-(4-chloro-α-chlorobenzylidene)imino-3-chloro-3-cephem-4-carboxylate from 4'-nitrobenzyl 7-(4-chlorobenzamido)-3-hydroxy-3-cephem-4-carboxylate; triphenyl phosphite.

EXAMPLE 55

4'-Nitrobenzyl 7-(1-bromo-2-phenylethylidene)imino-3-bromo-3-cephem-4-carboxylate from 4'-nitrobenzyl 7-phenylacetamido-3-hydroxy-3-cephem-4-carboxylate; triphenyl phosphite.

EXAMPLE 56

4'-Nitrobenzyl 7-phenoxyacetamido-3-bromo-3-cephem-4-carboxylate. Triphenyl phosphite-bromine.

To a solution of 2.30 ml (4.5 mmol) of bromine in 90 ml of methylene chloride at $-70°$ C. was added 12.22 ml (46.6 mmol) triphenyl phosphite to discharge the bromine color. To this solution was added 10.6 gm (20 mmol) of 4'-nitrobenzyl 7-phenoxyacetamido-3-hydroxy-3-cephem-4-carboxylate which was washed into the reaction mixture with 10 ml of methylene chloride. The mixture was warmed to $-35°$ to $-30°$ C., and a solution of 3.64 ml (45 mmol) of pyridine in 16 ml of methylene chloride was added dropwise over 35 minutes. After 4 hours 50 ml of ice water was added to the reaction mixture. The resulting solution was stirred for ½ hour. Three layers were noted. The methylene chloride layer, the middle layer, was washed with 50 ml of water and brine and the dried with anhydrous $Na_2SO_4$. The solvent was evaporated in vacuo to a weight of 29.7 grams. The addition of 150 ml of methanol induced crystallization of the titled product: 3.78 gm (dried); m.p. 138°-139° C.

nmr (DMSO d-6) δ4.0 (ABq, $C_2$-H), 4.65 (s, 2, side chain $CH_2$), 5.28 (d, 1, J=5 Hz), 5.47 (s, 2, ester $CH_2$), 5.8 (q, 1, J=5 Hz and 8 Hz) and 6.9-8.4 (ArH).

EXAMPLE 57

Benzyl 7-(1-chloro-2-phenylethylidene)-7-methoxy-3-acetoxymethyl-3-cephem-4-carboxylate.

To a solution of the triphenyl phosphite-chlorine complex prepared from chlorine and 12.3 mmol of triphenyl phosphite in the presence of 0.1 ml of pyridine in 45 ml of methylene chloride at $-15°$ C. were added 5.11 gm (10 mmol) of benzyl 7-phenylacetamido-7-methoxy-3-acetoxymethyl-3-cephem-4-carboxylate and dropwise over 10 minutes a solution of 1.01 ml (12.5 mmol) of pyridine in 4 ml of methylene chloride. After 50 minutes at $-15°$ to $-10°$ C., 2.1 ml (30 mmol) of propylene oxide was added. After and additional 10 minutes (reaction temperature to 0° C.), the reaction mixture was washed with 25 ml of ice water, dried over $CaCl_2$ and evaporated in vacuo to 11 gm of syrup. The product was triturated 3 times under carbon tetrachloride and then taken up in 50 ml of ether. The ethereal solution was decanted from 0.5 gm of precipitate and then evaporated in vacuo to about 25 ml. An oily product was obtained with the resulting ethereal solution was diluted with 25 ml of hexane. The oil was washed twice with 1:1/hexane:ether and then evaporated in vacuo twice from carbon tetrachloride solutions to a foam providing 2.5 gm of the title product.

ir ($CHCl_3$) 1780 and 1730 $cm^{-1}$.

nmr ($CDCl_3$, pyridine d-5) δ1.96 (s, 3), 3.3 (ABq), 3.43 (s, 2), 3.93 (s, 2), 4.86 (ABq), 4.93 (s, 1), 5.25 (s, 1) and 7.3 (ArH).

EXAMPLE 58

α-[3-Phenoxymethyl-7-oxo-2,6-diaza-4-thiabicyclo-[3.2.0]hept-2-en-6-yl]-α-(1-bromoethylidene)acetic acid.

(A) Under anhydrous conditions, 1.1 ml of bromine was added to a solution of 0.5 ml of pyridine in 70 ml of methylene chloride at $-20°$ C. Triphenyl phosphite (5.7 ml) was added to the reaction mixture to a colorless end point. To the resulting solution was added 7.04 gm of 4'-nitrobenzyl α-[3-phenoxymethyl-7-oxo-2,6-diaza-4-thiabicyclo[3.2.0]hept-2-en-6-yl]-α-(1-hydroxyethylidene)acetate. Over a 30-minute period, a solution of 1.12 ml of pyridine in 15 ml of methylene chloride was added. The reaction mixture was allowed to warm to 0° C. and stirred for about 15 hours. The mixture was then diluted with ethyl acetate and washed successively with 1 N. HCl and saturated sodium bicarbonate solution. The ethyl acetate solution was then dried over anhydrous magnesium sulfate and concentrated in vacuo. Chromatography of the crude product over silica gel using a 15 percent ethyl acetate/toluene eluent provided 3.2 gm of the titled product as a mixture of the cis and trans isomers.

nmr ($CDCl_3$) δ2.66 (s, 3, $CH_3$ trans to COOH); 2.80 (s, 3, $CH_3$ cis to COOH); 4.58 (s, 2, $C_6H_5OCH_2$); 5.35 (s, 2, ester $CH_2$); 6.06 (m, 2, β-lactam H) and 6.8–8.4 (ArH).

(B) A slurry of 3 gm of a 5% palladium/-carbon catalyst in ethanol was hydrogenated at 60 psi for ½ hour. A solution of the product from Paragraph A above in a 1:1-methanol:tetrahydrofuran mixture was added to the hydrogenated catalyst. The mixture was then hydrogenated at 60 psi for 1½ hours. The catalyst was filtered and the filtrate concentrated in vacuo to a red oil. This product was dissolved in ethyl acetate and extracted with aqueous sodium bicarbonate. The aqueous layer was separated and after the pH was adjusted to 6.8, it was extracted with ethyl acetate. The pH of the aqueous layer was then adjusted to 2.0 after which the aqueous layer was extracted with chloroform. Evaporation in vacuo of the chloroform extract gave 1.4 gm of the titled product.

nmr (CDCl₃) δ2.3 (s, 3, CH₃ trans to COOH), 2.83 (s, 3, CH₃ cis to COOH), 5.0 (s, 2, C₆H₅OC$\underline{H}$₂), 6.04 (m, 2, β-lactam H) and 6.8–7.4 (ArH).

EXAMPLE 59

α-[2-Benzyl-7-oxo-2,6-diaza-4-thiabicyclo[3.2.0]-hept-2-en-6-yl]-α-(1-bromoethylidene)acetic acid (A) A 250 ml 3-neck round-bottom flask equipped with a magnetic stirrer, serum cap, claisen head, gas inlet and thermometer was flame dried under a nitrogen current. The flask was charged with dry methylene chloride (175 ml) and dry pyridine (3.1 ml, 38.5 mmol) and cooled to −23° C. Bromine (2.0 ml, 38.5 mmol) was added, and the color was discharged by the dropwise addition of triphenyl phosphite (10.1 ml, 38.5 mmol). The substrate, 4′-nitrobenzyl α-[3-benzyl-7-oxo-2,6-diaza-4-thiabicyclo[3.2.0]hept-2-en-6-yl]-α-(1-hydroxyethylidene)acetate (35 mmol), was added in one portion. After one hour at −20° the reaction mixture was warmed to 0° C. and stirred for 24 hours. The mixture was then extracted sequentially with dilute HCl, saturated sodium bicarbonate solution, and brine. The organic phase was dried (magnesium sulfate) and concentrated in vacuo. A portion of the residual oil was chromatagraphed on a short silica gel column to afford 1.98 grams of the corresponding 1-bromoethylidene acetic acid 4′-nitrobenzyl ester as a mixture of isomers.

nmr (CHCl₃) δ2.15 (s), 2.77 (s), 3.75 (br, s), 3.87 (br, s), 5.28 (s), 5.78 (d, J=3), 5.96 (s) and 6.00 (d, J=3).

(B) A 250 ml pressure bottle was charged with 2.0 gm of 5% palladium on carbon and 20 ml of ethanol. The suspension was shaken under hydrogen pressure (60 psi) for ½ hour. The product from Paragraph A immediate above was dissolved in a THF/methanol-70:10 (80 ml) and added to the pre-reduced catalyst suspension. After shaking under hydrogen pressure (60 psi) for one hour, the catalyst was removed by filtration. The filtrate was concentrated to an oil and the partitioned between ethyl acetate and saturated sodium bicarbonate solution. The aqueous phase was adjusted to pH 6.8 and extracted with ethyl acetate. The aqueous phase was then brought to pH 2.2, and the product crystallized. The crystals were collected on a filter, washed with water, and dried in vacuo to yield 814 mg (56 percent) of the title product.

ir (KBr) 1760, 1705, 1595, 1358, 1220, 1028 and 695 cm⁻¹.

nmr (CDCl₃) δ2.00 (s), 2.62 (s), 3.81 (s), 3.83 (s), 5.87 (d, J=3), 5.96 (s), 6.05 (d, J=3) and 7.20 (s).

EXAMPLE 60

α-[3-Phenoxymethyl-7-oxo-2,6-diaza-4-thiabicyclo-[3.2.0]hept-2-en-6-yl]-α-(1-chloroethylidene)acetic acid (A) A 250 ml 3-neck round-bottom flask equipped with a magnetic stirrer, serum cap, stopper, claisen head, gas inlet tube and thermometer was flame dried under a nitrogen current and cooled to room temperature. Chlorine gas was bubbled through dry methylene chloride (100 ml) at −25° C. and the yellow color was titrated to a colorless endpoint with triphenyl phosphite (7.2 ml, 25 mmol). This substrate, 4′-nitrobenzyl α-[3-phenoxymethyl-7-oxo-2,6-diaza-4-thiabicyclo[3.2.0-]hept-2-en-6-yl]-α-(1-hydroxyethyl-idene)acetate (9.39 gm, 20 mmol), was added in one portion with 5 ml of dry methylene chloride to aid the transfer. The reaction mixture was warmed to −10° C. and dry pyridine (2.02 ml, 25 mmol) was added dropwise over ½ hour in dry methylene chloride. The system was warmed to 0° over 35 minutes and then poured into 1:1 (v/v) of 0.5 N HCl:saturated sodium chloride. The aqueous phase was washed with methylene chloride and the combined organic extracts were dried (magnesium sulfate) and concentrated to afford a mixture of the desired 4′-nitrobenzyl ester of the title product and triphenyl phosphite.

(B) The unpurified vinyl chloride 4′-nitrobenzyl ester from Paragraph A was hydrogenated at 60 psi in a Parr apparatus with 9 gm of 5% palladium on charcoal (pre-reduced) in 200 ml of 1:1-methanol:-ethanol. The catalyst was filtered, and the resulting clear solution was concentrated to an orange oil. This oil was taken up in ethyl acetate and layered with a saturated sodium bicarbonate solution. The aqueous phase was extracted with a second portion of ethyl acetate. The pH of the aqueous phase was adjusted to 5.8 with concentrated HCl, and the aqueous phase was then extracted with ethyl acetate. The aqueous phase was carefully acidified to pH 2 at which point the product oiled from solution. The mixture was partitioned between methylene chloride and its aqueous phase. The organic phase was separated, dried (magnesium sulfate), and concentrated in vacuo. The resulting yellow oil was crystallized from ethyl acetate to yield the titled product.

ir (KBr) 1770, 1700, 1620, 1602, 1498, 1243, 1010, and 750 cm⁻¹.

nmr (DMSO-d₆) δ2.00 (s, 3), 5.02 (br, s, 2), 5.95 (d, 1, J=2 Hz), 6.16 (br, d, 1, J=2), 6.7-7.4 (m, 5).

Mass spectrum (EI) P+m/e=352, 354.

Anal calcd. for C₁₅H₁₃N₂O₄SCl: C, 51.07; H, 3.71; N, 7.94; S, 9.09; Cl, 10.05. Found: C, 50.85; H, 3.69; N, 7.92; S, 8.86; Cl, 10.28.

EXAMPLE 61

α-[3-Benzyl-7-oxo-2,6-diaza-4-thiabicyclo[3.2.0]hept-2-en-6-yl]-α-(1-chloroethylidene)acetic acid (A) A 250 ml three-neck round-bottom flask equipped with a magnetic stirrer, claisen-head, thermometer, gas inlet stopper, and serum cap was flame dried under a nitrogen current and then cooled to room temperature. Chlorine gas was bubbled through dry methylene chloride (50 ml) at −20° C., and the yellow color was titrated with triphenyl phosphite (3.7 ml, 13 mmol). The substrate, 4′-nitrobenzyl α-[3-benzyl-7-oxo-2,6-diaza-4-thiabicyclo[3.2.0]hept-2-en-6-yl]-α-(1-hydroxyethylidene)acetate (4.54 gm, 10 mmol) was added with methylene chloride (5 ml) to aid the transfer. After warming to −10° C., dry pyridine (1.1 ml, 13 mmol) was added in methylene chloride (10 ml) over the course of 40 minutes. The system was warmed to 0° over 20 minutes, and then it was extracted with 0.1 N HCl. The organic phase was dried (magnesium sulfate) and concentrated in vacuo to give an orange oil. This crude material, shown by nmr and thin-layer chromatographic analysis to contain a mixture of the desired product and triphenyl phosphate, was used directly in the ester removal described in paragraph B below.

nmr (CDCl₃) δ1.97 (s, 3); 3.85 (s, 2); 5.25 (s, 2); 5.80 (d, 1, J=2 Hz); 5.98 (br, d, 1, J=2 Hz).

(B) A Parr apparatus pressure bottle was charged with methanol (40 ml) and 5% palladium on charcoal (4.0 gm). The system was shaken to equilibrium with hydrogen at 60 psi for one hour. The crude vinyl chloride 4′-nitrobenzyl ester from Paragraph A immediately above was added to the catalyst slurry, and the system was hydrogenated at 60 psi for 1½ hours. The catalyst was filtered, and the filtrate was concentrated in vacuo. The resulting bright yellow oil was dissolved in ethyl acetate and layered with water. After adjusting pH to 6.6 with 1 N. sodium hydroxide solution, the organic phase was separated. The pH was adjusted to 2, and a yellow solid precipitated. The solid was collected on a filter, washed with water, and dried in vacuo to afford 2.4 gm (71%) of the cis-isomer of the titled acid.

ir (KBr) 3020, 1760, 1722, 1498, 1459, 1362, 1225, 1148, 1071, and 1027 cm$^{-1}$.

nmr (DMSO-$d_6$) $\delta$1.87 (s, 3); 3.90 (s, 2); 5.93 (d, 1, J=2 Hz), 6.11 (br, d, 1, J=2 Hz) and 7.24 (s, 5).

EXAMPLE 62

4'-Nitrobenzyl 7-amino-3-chloro-3-cephem-4-carboxylate hydrochloride using tri(p-chlorophenyl)-phosphite-chlorine kinetic complex.

To 10.34 gm of tri(p-chlorophenyl)phosphite and 0.53 ml (6.5 mmol) of pyridine in 50 ml of methylene chloride at −70° C. was added chlorine in 15 ml of methylene chloride. Amylene (0.52 ml) was added to discharge excess chlorine. To the resulting solution of the tri(p-chlorophenyl) phosphite-chlorine complex was added of 4'-nitrobenzyl 7-phenoxyacetamido-3-hydroxy-3-cephem-4-carboxylate (5.28 gm) using 10 ml of methylene chloride to wash the substrate into the reaction mixture. Then 1.57 ml (19.5 mmol) of pyridine in 9 ml of methylene chloride was added dropwise over 33 minutes. After 2 hours the reaction mixture was allowed to warm to 2° C. Isobutanol (6.94 ml) was added, and HCl gas was bubbled through the mixture for 2 minutes. The mixture was evaporated in vacuo to a syrup to which was added 50 ml of ethyl acetate. The gum was triturated with about 100 ml of methanol. A white solid, tri(p-chlorophenyl)phosphate, was filtered. The filtrate was evaporated in vacuo to dryness. To the residue were added 15 ml of 1:1-toluene/ethyl acetate and just enough methanol to dissolve the gummy residue. Upon standing for about 5 minutes, 0.97 gm of the titled product crystallized as a white solid. m.p. 184°–186° C. (dec.).

We claim:

1. A process for preparing a compound of the formula

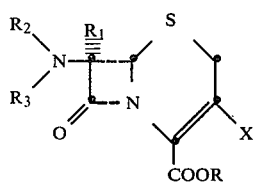

which comprises reacting a compound of the formula

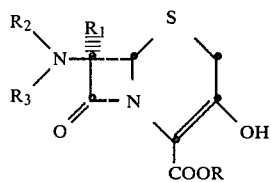

with about 1.0 to about 1.3 equivalents of a halogenating compound of the formula

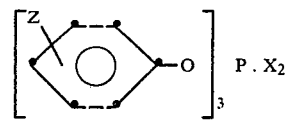

which is the kinetically controlled product of the reaction, in a substantially anhydrous inert organic solvent, of equivalent amounts of a triaryl phosphite of the formula

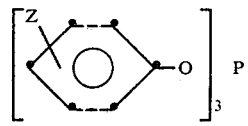

and chlorine or bromine,
in a substantially anhydrous inert organic solvent at a temperature below about 30° C. wherein in the above formulas X is Cl or Br;
Z is hydrogen, halo, $C_1$-$C_4$ alkyl or $C_1$-$C_4$ alkoxy;
R is carboxylic acid protecting group;
$R_1$ is hydrogen or methoxy; and

is amino protected by a conventional amino protecting group; or
$R_2$ is hydrogen or an acyl group derived from a carboxylic acid; and
$R_3$ is an acyl group derived from a carboxylic acid; or
$R_2$ and $R_3$ taken together with the nitrogen atom to which they are attached form a group of the formula

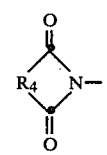

wherein $R_4$ is the residue of an acyl group derived from a dicarboxylic acid; provided that when $R_2$ and $R_3$ are substituted by amino, hydroxy or carboxy groups, those groups are first protected by one of the conventional amino, hydroxy or carboxy protecting groups.

2. The process of claim 1 wherein $R_2$ is hydrogen and $R_3$ is an acyl group derived from a carboxylic acid.

3. The process of claim 1 wherein $R_1$ is hydrogen.

4. The process of claim 1 wherein Z is hydrogen, methoxy, methyl or chloro.

5. The process of claim 4 wherein Z is hydrogen.

6. The process of claim 4 wherein X is Cl.

7. The process of claim 5 wherein X is Br.

8. The process of claim 1 wherein $R_1$ is hydrogen X is Cl and Z is hydrogen.

9. A process for preparing a compound of the formula

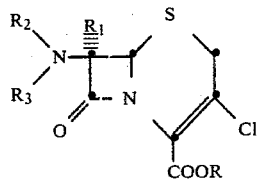

which comprises reacting a compound of the formula

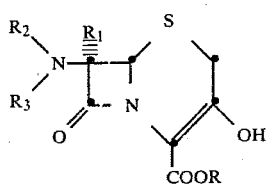

with about 1.0 to about 1.3 equivalents of a chlorinating compound of the formula

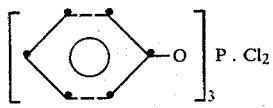

which
(a) has a $^{31}$P nuclear magnetic resonance signal in methylene chloride at $-3.7$ ppm relative to that of phosphoric acid;
(b) has in methylene chloride an infrared spectrum which has the following characteristic absorptions: 1120–1190 (very strong), 1070 (very strong), 1035 (strong), 1010 (very strong), 990 (very strong), 640 (medium) 625 (medium), 580 (weak), 510 (strong) and 465 (weak);
(c) reacts with water to give HCl and triphenyl phosphate; and
(d) reacts with n-butanol to give HCl, n-butyl chloride, and triphenyl phosphate;
in a substantially anhydrous inert organic solvent at a temperature below about 30° C. wherein in the above formulas
R is a carboxylic acid protecting group;
R$_1$ is hydrogen or methoxy; and

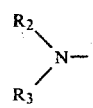

amino protecting group; or
R$_2$ is hydrogen or an acyl group derived from a carboxylic acid; and
R$_3$ is an acyl group derived from a carboxylic acid; or
R$_2$ and R$_3$ taken together with the nitrogen atom to which they are attached form a group of the formula

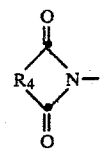

wherein R$_4$ is the residue of an acyl group derived from a dicarboxylic acid; provided that when R$_2$ and R$_3$ are substituted by amino, hydroxy or carboxy groups, those groups are first protected by one of the conventional amino, hydroxy or carboxy protecting groups.

10. The process of claim 1, claim 8, or claim 9 wherein the process is carried out in the presence of about 1.0 to about 1.2 equivalents of a tertiary amine base per equivalent of halogenating agent.

11. The process of claim 10 wherein the tertiary amine base has a pK$_b$ value of about 6 to about 10.

12. The process of claim 10 wherein the tertiary amine base is pyridine.

13. The process of claim 11 wherein the temperature is about 0° to about $-70°$ C.

14. The process of claim 13 wherein the inert organic solvent is an aromatic hydrocarbon or a halogenated hydrocarbon.

15. The process of claim 10 wherein the halogenating compound employed is stabilized with a tertiary amine base.

16. A process for preparing an imino halide compound of the formula

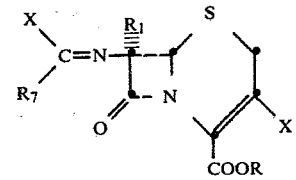

which comprises reacting a compound of the formula

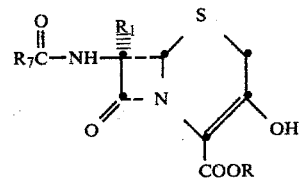

with about 2.0 to about 3.0 equivalents of a halogenating compound of the formula

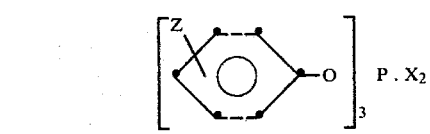

which is the kinetically controlled product of the reaction, in a substantially anhydrous inert organic solvent, of equivalent amounts of a triaryl phosphite of the formula

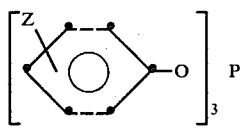

and chlorine or bromine, in the presence of about 1.0 to about 1.2 equivalent of a tertiary amine base per equivalent of halogenating compound employed, in a substantially anhydrous inert organic solvent at a temperature below about 30° C. wherein the above formulas X is Cl or Br;

Z is hydrogen, halo, $C_1$-$C_4$ alkyl or $C_1$-$C_4$ alkoxy;

R is a carboxylic acid protecting group;

$R_1$ is hydrogen or methoxy;

and $R_7$ is the residue of an acyl group derived from a carboxylic acid; provided that when $R_7$ is substituted by amino, hydroxy or carboxy groups, those groups are first protected by one of the conventional amino, hydroxy, or carboxy protecting groups.

17. The process of claim 16 wherein Z is hydrogen, methoxy, methyl or chloro.

18. The process of claim 16 wherein Z is hydrogen.

19. The process of claim 18 wherein $R_1$ is hydrogen.

20. The process of claim 19 wherein X is Br.

21. The process of claim 19 wherein X is Cl.

22. A process for preparing an imino halide compound of the formula

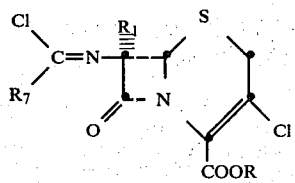

which comprises reacting a compound of the formula

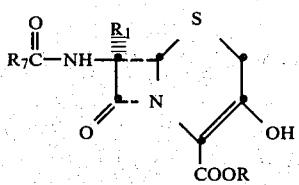

with about 2.0 to about 3.0 equivalents of chlorinating compound of the formula

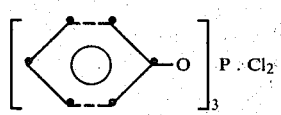

which
(a) has a $^{31}P$ nuclear magnetic resonance signal in methylene chloride at $-3.7$ ppm relative to that of phosphoric acid;
(b) has in methylene chloride an infrared spectrum which has the following characteristic absorptions: 1120–1190 (very strong), 1070 (very strong), 1035 (strong), 1010 (very strong), 990 (very strong), 640 (medium) 625 (medium), 580 (weak), 510 (strong) and 465 (weak);
(c) reacts with water to give HCl and triphenyl phosphate; and
(d) reacts with n-butanol to give HCl, n-butyl chloride, and triphenyl phosphate;

in the presence of about 1.0 to about 1.2 equivalent of a tertiary amine base per equivalent of chlorinating compound employed, in a substantially anhydrous inert organic solvent at a temperature below about 30° C. wherein in the above formulas R is a carboxylic acid protecting group;

$R_1$ is hydrogen or methoxy;

and $R_7$ is the residue of an acyl group derived from a carboxylic acid; provided that when $R_7$ is substituted by amino, hydroxy or carboxy groups, those groups are first protected by one of the conventional amino, hydroxy, or carboxy protecting groups.

23. The process of claim 22 wherein $R_1$ is methoxy.

24. The process of claim 22 wherein $R_1$ is hydrogen.

25. The process of claim 21, claim 22 or claim 24 wherein the group $R_7$ CONH— is a conventional cephalosporin or penicillin acylamino group.

26. The process of claim 25 wherein the tertiary amine base has a $pK_b$ value of about 6 to about 10.

27. The process of claim 26 wherein about 2.2 to about 2.4 equivalents of halogenating compound are employed.

28. The process of claim 27 wherein the halogenating compound is stabilized with a tertiary amine base.

29. The process of claim 28 wherein after the formation of the imino chloride product is complete, an excess of a $C_1$-$C_{15}$ aliphatic alcohol and hydrogen chloride are added to the reaction mixture to provide a nucleus hydrochloride of the formula

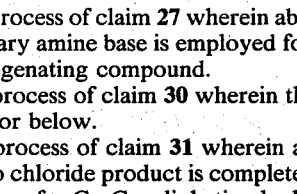

30. The process of claim 27 wherein about 1.0 equivalent of tertiary amine base is employed for each equivalent of halogenating compound.

31. The process of claim 30 wherein the temperature is about 0° or below.

32. The process of claim 31 wherein after formation of the imino chloride product is complete, at least about 3-fold excess of a $C_1$-$C_{15}$ aliphatic alcohol and hydrogen chloride are added to the reaction mixture to provide a nucleus ester hydrochloride of the formula 33. The process of claim 34 wherein about 2.3 equivalents of the halogenating compound and about 2.3 equivalents of pyridine are employed at a temperature of about $-10°$ to about $-70°$ C.

34. The process of claim 33 wherein after formation of the imino chloride product is complete, about 3 to about 15 equivalents of a $C_4$-$C_{12}$ β-disubstituted primary aliphatic alcohol, a $C_2$-$C_{12}$ 1,2-diol or a $C_3$-$C_{15}$ 1,3-diol and hydrogen chloride are added to the reaction mixture to provide a nucleus ester hydrochloride of the formula

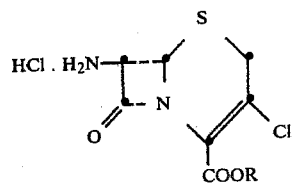

35. The process of claim 34 wherein the alcohol or diol employed is isobutanol, 1,3-propanediol, or 1,2-propanediol.

36. The process of claim 34 wherein the inert organic solvent is an aromatic hydrocarbon or a halogenated hydrocarbon.

37. The process of claim 36 wherein $R_7$ is benzyl, phenoxymethyl or 2-thienylmethyl.

38. The process of claim 37 wherein R is 4-nitrobenzyl.

* * * * *

UNITED STATES PATENT AND TRADEMARK OFFICE
CERTIFICATE OF CORRECTION

PATENT NO. : 4,226,986
DATED : October 7, 1980
INVENTOR(S) : Lowell D. Hatfield et al.

It is certified that error appears in the above-identified patent and that said Letters Patent are hereby corrected as shown below:

Column 3, line 2, "the tiaryl" should read --the triaryl--.

Column 3, line 16, "(p-chlorophenyl)-phosphite" should read --(p-chlorophenyl)phosphite--.

Column 3, line 19, "tri-(p-n-propylphenyl)" should read --tri(p-n-propylphenyl)--.

Column 3, line 20, "phenyl)-phosphite," should read --phenyl)phosphite--.

Column 5, line 5, "and (PhP)" should read --and (PhO)--.

Column 10, line 43, "is a diacyl group derived from a" should read --from a--.

Column 14, line 19, "of halogenated" should read --or halogenated--.

Column 18, line 11, "50 ml An" should read --50 ml. An--.

Column 20, line 27, "about 20 for" should read --about 20° for--.

UNITED STATES PATENT AND TRADEMARK OFFICE
CERTIFICATE OF CORRECTION

PATENT NO. : 4,226,986

DATED : October 7, 1980

INVENTOR(S) : Lowell D. Hatfield et al.

It is certified that error appears in the above-identified patent and that said Letters Patent are hereby corrected as shown below:

Column 33, lines 54-60,

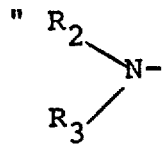

amino protecting group; or" should read

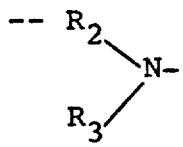

is amino protected by a conventional amino protecting group; or--.

Column 35, line 12, "wherein the" should read --wherein in the--.

Signed and Sealed this

Twelfth Day of May 1981

[SEAL]

Attest:

RENE D. TEGTMEYER

Attesting Officer

Acting Commissioner of Patents and Trademarks